(12) United States Patent
Leven (10) Patent No.: US 9,504,839 B2
(45) Date of Patent: Nov. 29, 2016

(54) TENSION CLAMP SIDE LOADING LEAD ANCHOR AND METHODS AND SYSTEMS USING THE LEAD ANCHOR

(71) Applicant: BOSTON SCIENTIFIC NEUROMODULATION CORPORATION, Valencia, CA (US)

(72) Inventor: Jacob B. Leven, Huntington Beach, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 203 days.

(21) Appl. No.: 14/326,233

(22) Filed: Jul. 8, 2014

(65) Prior Publication Data

US 2015/0018916 A1    Jan. 15, 2015

Related U.S. Application Data

(60) Provisional application No. 61/846,476, filed on Jul. 15, 2013.

(51) Int. Cl.
*A61N 1/375* (2006.01)
*A61N 1/05* (2006.01)

(52) U.S. Cl.
CPC .......... *A61N 1/3752* (2013.01); *A61N 1/0553* (2013.01); *A61N 1/0558* (2013.01); *A61N 1/375* (2013.01)

(58) Field of Classification Search
CPC .. A61N 1/375; A61N 1/3752; A61N 1/3758; A61N 1/3968; A61N 1/0558; A61N 1/0553
USPC ............................................ 607/116, 36, 37
See application file for complete search history.

(56) References Cited

U.S. PATENT DOCUMENTS

| | | |
|---|---|---|
| 5,957,968 A | 9/1999 | Belden et al. |
| 6,181,969 B1 | 1/2001 | Gord |
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 7,244,150 B1 | 7/2007 | Brase et al. |
| 7,437,193 B2 | 10/2008 | Parramon et al. |
| 7,672,734 B2 | 3/2010 | Anderson et al. |
| 7,761,165 B1 | 7/2010 | He et al. |
| 7,949,395 B2 | 5/2011 | Kuzma |
| 7,974,706 B2 | 7/2011 | Moffitt et al. |
| 8,175,710 B2 | 5/2012 | He |

(Continued)

*Primary Examiner* — Christopher D Koharski
*Assistant Examiner* — Michael Carey
(74) *Attorney, Agent, or Firm* — Lowe Graham Jones PLLC; Bruce E. Black (57) ABSTRACT

An implantable lead anchor includes a first anchor shell having a first hinge element and a second anchor shell, disposed opposite the first anchor shell, having a second hinge element. The first and second anchor shells define a lead channel and the first and second hinge elements form a hinge. The lead anchor includes at least one tensioning element that is configured and arranged to increase in tension upon elongation. The first and second anchor shells, and the tensioning element provide an open position and a closed position. In the open position, a lead can be side loaded side loaded into the lead channel. In the closed position, the first and second anchor shells grip a portion of the lead disposed in the lead channel and, in combination with the at least one tensioning element, resist disengagement of the lead from the lead anchor.

20 Claims, 9 Drawing Sheets

(56) References Cited

U.S. PATENT DOCUMENTS

| | | |
|---|---|---|
| 8,224,450 B2 | 7/2012 | Brase |
| 8,364,278 B2 | 1/2013 | Pianca et al. |
| 2007/0150036 A1 | 6/2007 | Anderson |
| 2009/0233491 A1* | 9/2009 | Barker ............... A61N 1/3752 439/668 |
| 2011/0288618 A1 | 11/2011 | Glen et al. |

* cited by examiner

TENSION CLAMP SIDE LOADING LEAD ANCHOR AND METHODS AND SYSTEMS USING THE LEAD ANCHOR

CROSS-REFERENCE TO RELATED APPLICATIONS

This application claims the benefit under 35 U.S.C. §119 (e) of U.S. Provisional Patent Application Ser. No. 61/846,476, filed Jul. 15, 2013, which is incorporated herein by reference.

FIELD

The present invention is directed to the area of implantable electrical stimulation systems and methods of making and using the systems. The present invention is also directed to lead anchors for implantable electrical stimulation leads as well as methods of making and using the lead anchors with leads and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue. A lead anchor is often used to anchor the lead, thereby providing sufficient grip to the lead in order to keep the lead in a correct position with respect to the patient.

BRIEF SUMMARY

One embodiment is an implantable lead anchor that includes a first anchor shell having a first hinge element and a second anchor shell, disposed opposite the first anchor shell, having a second hinge element. The first and second anchor shells define a lead channel between the first and second anchor shells. The first and second hinge elements form a hinge. The lead anchor also includes at least one tensioning element coupled to the first and second anchor shells and each of the at least one tensioning element is configured and arranged to increase in tension upon elongation. The first and second anchor shells and the at least one tensioning element provide an open position and a closed position. In the open position, a lead can be side loaded into the lead channel. In the closed position, the first and second anchor shells grip a portion of the lead disposed in the lead channel and, in combination with the at least one tensioning element, resist disengagement of the lead from the lead anchor. The lead anchor is configured and arranged to move between the open position and the closed position using the hinge. The lead anchor further defines an intermediate position between the open position and the closed position in which, in the intermediate position, the at least one tensioning element is more elongated than in both the open position and the closed position.

Another embodiment is a kit including the implantable lead anchor described above and at least one electrical stimulation lead. The implantable lead anchor is configured and arranged to receive a portion of one of the at least one electrical stimulation lead in the lead channel.

A further embodiment is a method of implanting an electrical stimulation lead. The method includes side loading a portion of an electrical stimulation lead into the lead channel of the implantable lead anchor described above, with the first and second anchor shells of the implantable lead anchor in the open position. The method includes closing the first and second anchor shells to the closed position to lock the first electrical stimulation lead in the implantable lead anchor.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed leads anchors for use with implantable electrical stimulation leads, as well as methods of making and using the lead anchors, the leads and electrical stimulation systems.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated by reference.

Figure 1:
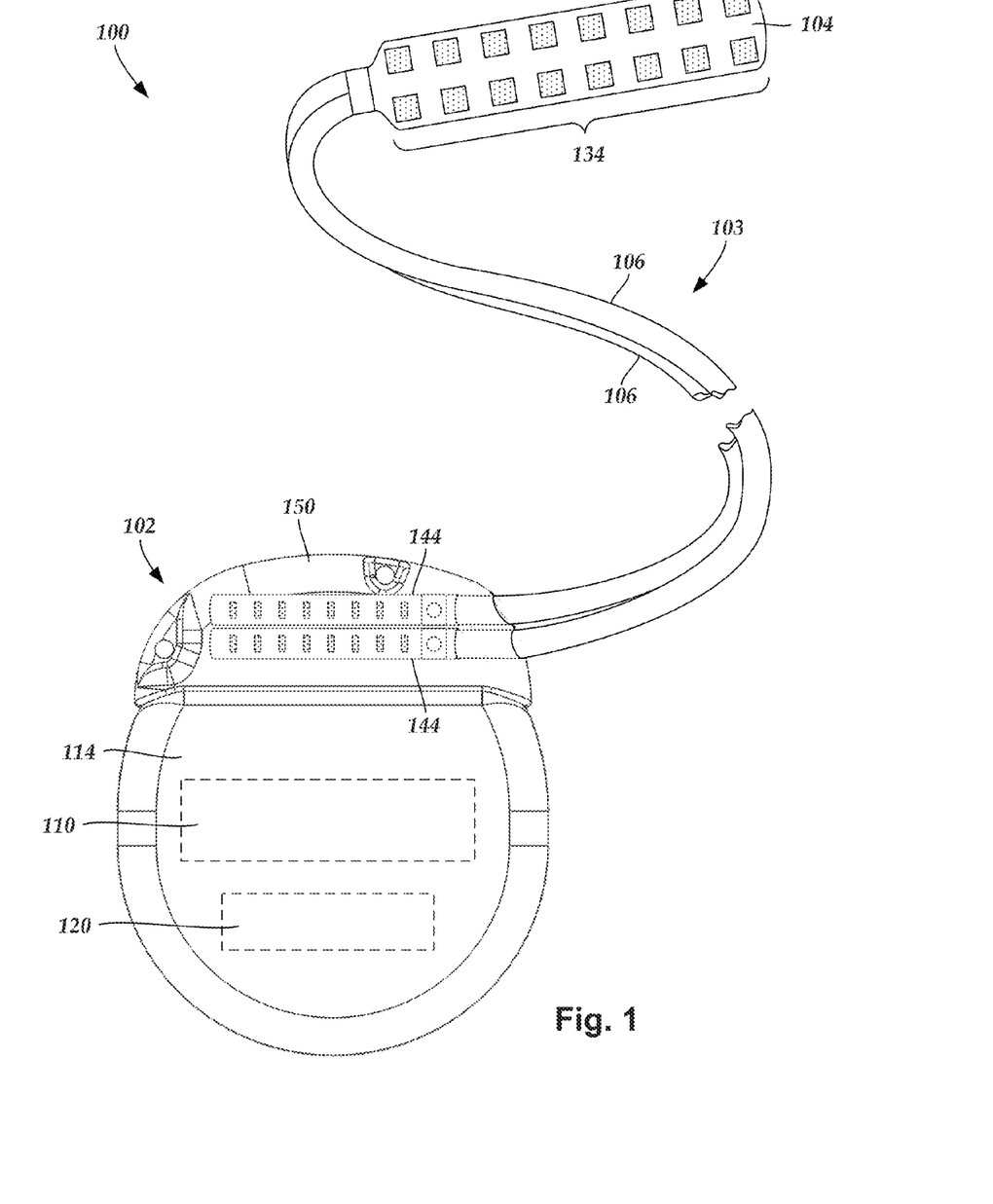
FIG. 1 is a schematic view of one embodiment of an electrical stimulation system that includes a paddle lead electrically coupled to a control module, according to the invention.
Figure 2:
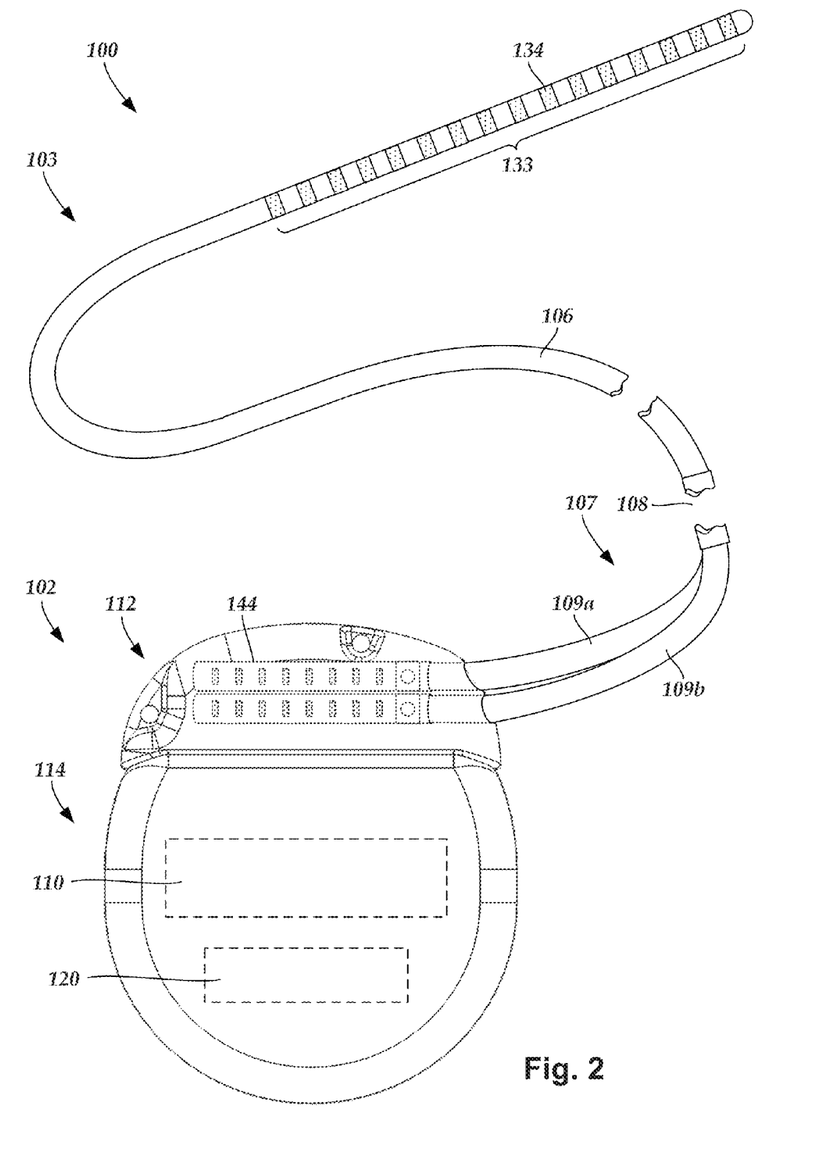
FIG. 2 is a schematic side view of one embodiment of an electrical stimulation system that includes a percutaneous lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array of electrodes 133, such as electrode 134, is disposed on the paddle body 104, and an array of terminals (e.g., 210 in FIG. 2A-2B) is disposed along each of the one or more lead bodies 106.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

FIG. 2 illustrates schematically another embodiment of the electrical stimulation system 100, where the lead 103 is a percutaneous lead. In FIG. 2, the electrodes 134 are shown disposed along the one or more lead bodies 106. In at least some embodiments, the lead 103 is isodiametric along a longitudinal length of the lead body 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices (300 in FIGS. 3A-3B). For example, in at least some embodiments one or more lead extensions 324 (see e.g., FIG. 3B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 2, the electrical stimulation system 100 is shown having a splitter 207 configured and arranged for facilitating coupling of the lead 103 to the control module 102. The splitter 207 includes a splitter connector 208 configured to couple to a proximal end of the lead 103, and one or more splitter tails 209a and 209b configured and arranged to couple to the control module 102 (or another splitter, a lead extension, an adaptor, or the like).

The control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the lead including, for example, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes of the paddle body 104 (or one or more lead bodies 106) are typically disposed in, or separated by, a non-conductive, biocompatible material such as, for example, silicone, polyurethane, polyetheretherketone ("PEEK"), epoxy, and the like or combinations thereof. The one or more lead bodies 106 and, if applicable, the paddle body 104 may be formed in the desired shape by any process including, for example, molding (including injection molding), casting, and the like. The non-conductive material typically extends from the distal ends of the one or more lead bodies 106 to the proximal end of each of the one or more lead bodies 106.

In the case of paddle leads, the non-conductive material typically extends from the paddle body 104 to the proximal end of each of the one or more lead bodies 106. Additionally, the non-conductive, biocompatible material of the paddle body 104 and the one or more lead bodies 106 may be the same or different. Moreover, the paddle body 104 and the one or more lead bodies 106 may be a unitary structure or can be formed as two separate structures that are permanently or detachably coupled together.

Figure 3A:
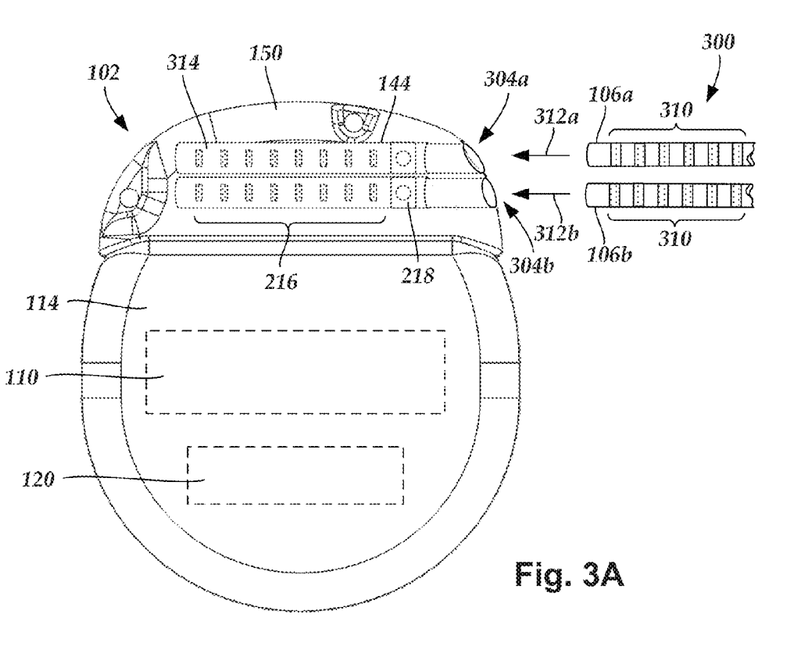
FIG. 3A is a schematic side view of one embodiment of the control module of FIG. 1 configured and arranged to electrically couple to an elongated device, according to the invention.
Figure 3B:
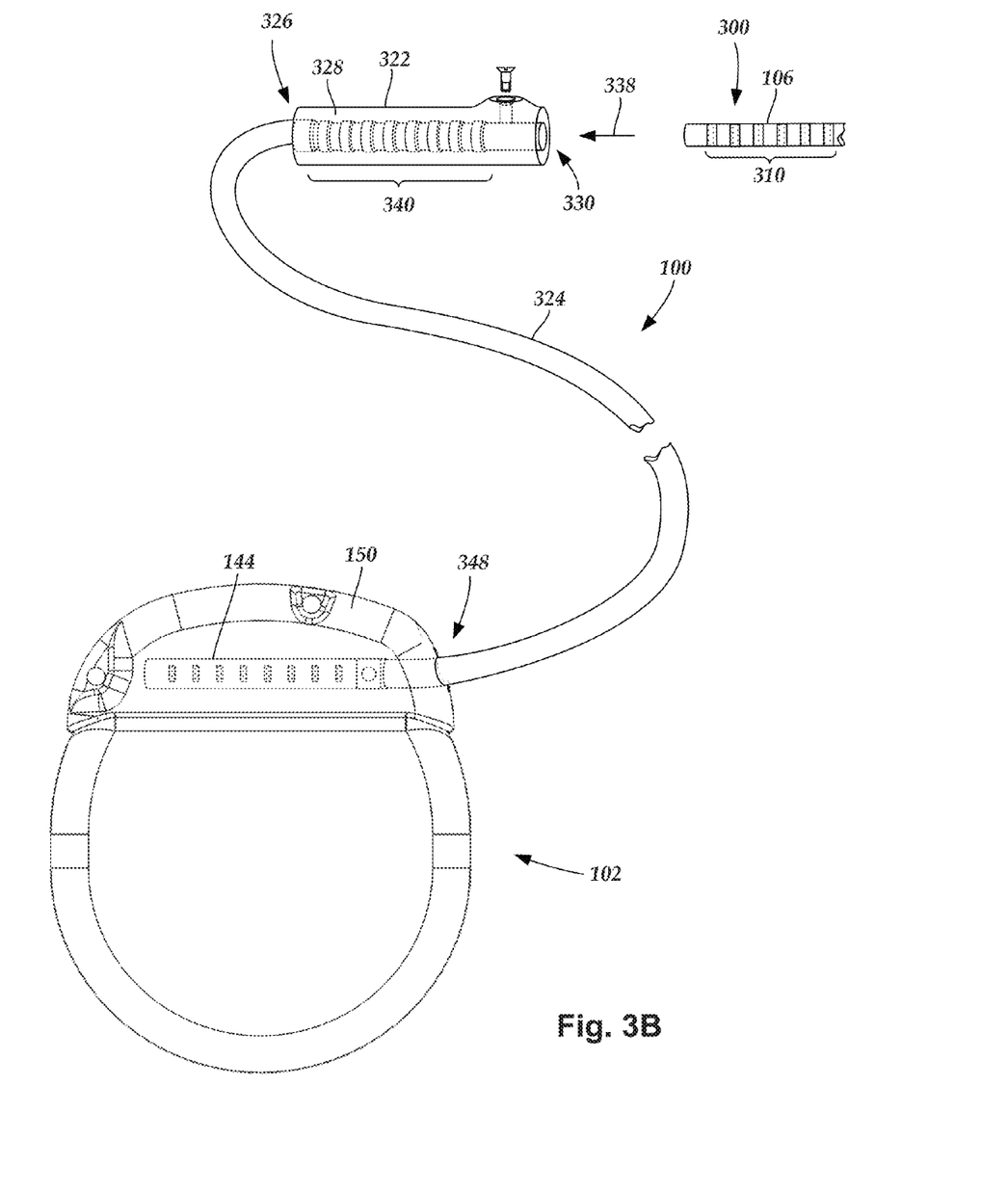
FIG. 3B is a schematic side view of one embodiment of a lead extension configured and arranged to electrically couple the elongated device of FIG. 2 to the control module of FIG. 1, according to the invention.

Terminals (e.g., 310 in FIGS. 3A-3B) are typically disposed along the proximal end of the one or more lead bodies 106 of the electrical stimulation system 100 (as well as any splitters, lead extensions, adaptors, or the like) for electrical connection to corresponding connector contacts (e.g., 314 in FIGS. 3A-3B). The connector contacts are disposed in connectors (e.g., 144 in FIGS. 1-3B; and 322

FIG. 3B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 3A is a schematic side view of one embodiment of a proximal end of one or more elongated devices 300 configured and arranged for coupling to one embodiment of the control module connector 144. The one or more elongated devices may include, for example, one or more of the lead bodies 106 of FIG. 1, one or more intermediate devices (e.g., a splitter, the lead extension 324 of FIG. 3B, an adaptor, or the like or combinations thereof), or a combination thereof.

The control module connector 144 defines at least one port into which a proximal end of the elongated device 300 can be inserted, as shown by directional arrows 312a and 312b. In FIG. 3A (and in other figures), the connector housing 112 is shown having two ports 304a and 304b. The connector housing 112 can define any suitable number of ports including, for example, one, two, three, four, five, six, seven, eight, or more ports.

The control module connector 144 also includes a plurality of connector contacts, such as connector contact 314, disposed within each port 304a and 304b. When the elongated device 300 is inserted into the ports 304a and 304b, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

FIG. 3B is a schematic side view of another embodiment of the electrical stimulation system 100. The electrical stimulation system 100 includes a lead extension 324 that is configured and arranged to couple one or more elongated devices 300 (e.g., one of the lead bodies 106 of FIGS. 1 and 2, the splitter 207 of FIG. 2, an adaptor, another lead extension, or the like or combinations thereof) to the control module 102. In FIG. 3B, the lead extension 324 is shown coupled to a single port 304 defined in the control module connector 144. Additionally, the lead extension 324 is shown configured and arranged to couple to a single elongated device 300. In alternate embodiments, the lead extension 324 is configured and arranged to couple to multiple ports 304 defined in the control module connector 144, or to receive multiple elongated devices 300, or both.

A lead extension connector 322 is disposed on the lead extension 324. In FIG. 3B, the lead extension connector 322 is shown disposed at a distal end 326 of the lead extension 324. The lead extension connector 322 includes a connector housing 328. The connector housing 328 defines at least one port 330 into which terminals 310 of the elongated device 300 can be inserted, as shown by directional arrow 338. The connector housing 328 also includes a plurality of connector contacts, such as connector contact 340. When the elongated device 300 is inserted into the port 330, the connector contacts 240 disposed in the connector housing 328 can be aligned with the terminals 310 of the elongated device 300 to electrically couple the lead extension 324 to the electrodes (134 of FIGS. 1 and 2) disposed along the lead (103 in FIGS. 1 and 2).

In at least some embodiments, the proximal end of the lead extension 324 is similarly configured and arranged as a proximal end of the lead 103 (or other elongated device 300). The lead extension 324 may include a plurality of electrically conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed along the proximal end 348 of the lead extension 324. In at least some embodiments, the proximal end 348 of the lead extension 324 is configured and arranged for insertion into a connector disposed in another lead extension (or another intermediate device). In other embodiments (and as shown in FIG. 3B), the proximal end 348 of the lead extension 324 is configured and arranged for insertion into the control module connector 144.

A lead can be anchored in patient tissue using a lead anchor. More particularly, a lead anchor can be designed so that the lead is side loaded into the lead anchor in contrast to many conventional lead anchors that are slid onto the lead starting at either a proximal end or distal end of the lead. In such proximally or distally loaded lead anchors, it may be difficult to slide a lead anchor along the lead (or vice versa). The side loading aspect is particularly advantageous for leads that are not isodiametric or which are bifurcated, branched or have other non-linear configuration(s). A side loaded lead anchor can be designed to be robust such that the lead anchor is prevented from closing and/or opening on its own.

Figure 4A:
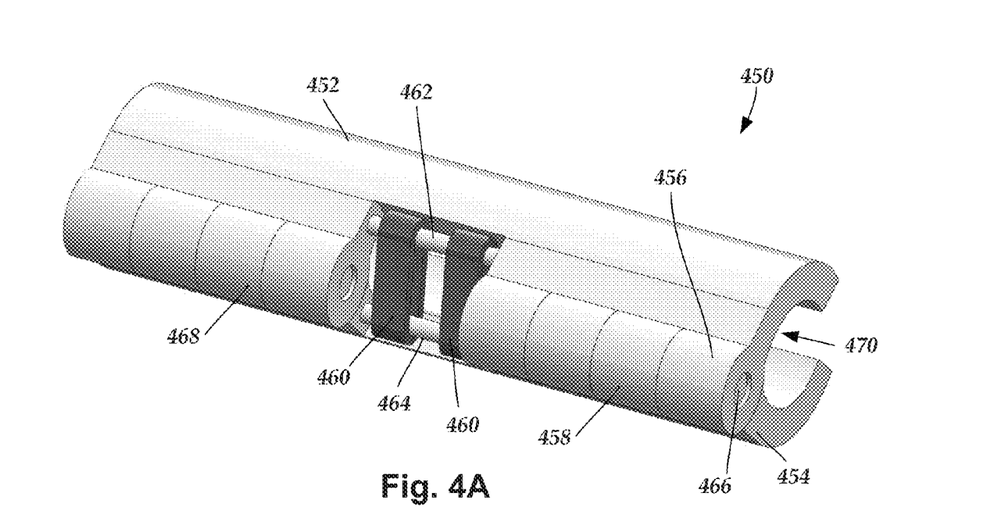
FIG. 4A is a schematic rear perspective view of one embodiment of a lead anchor with tensioning elements in a closed position, according to the invention.
Figure 4B:
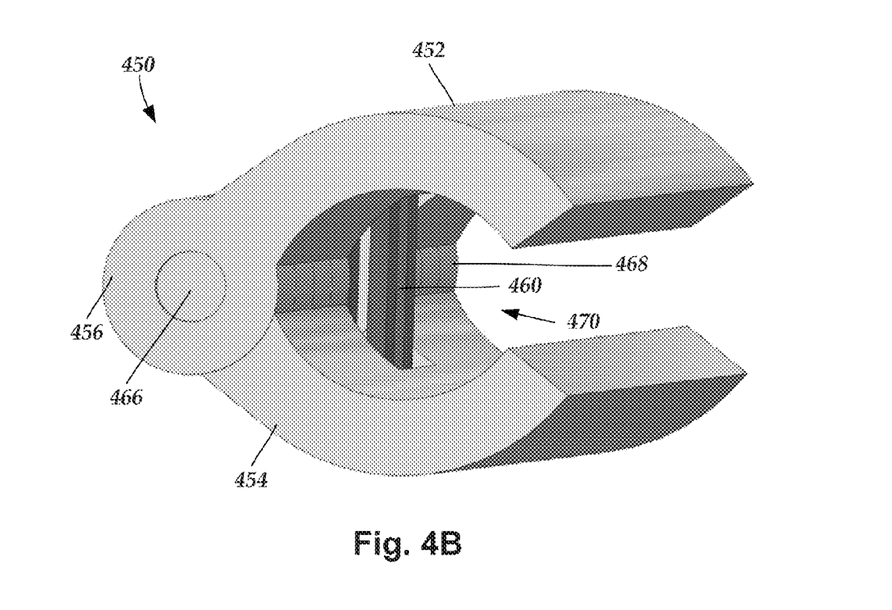
FIG. 4B is a schematic side perspective view of the lead anchor of FIG. 4A, according to the invention.
Figure 4C:
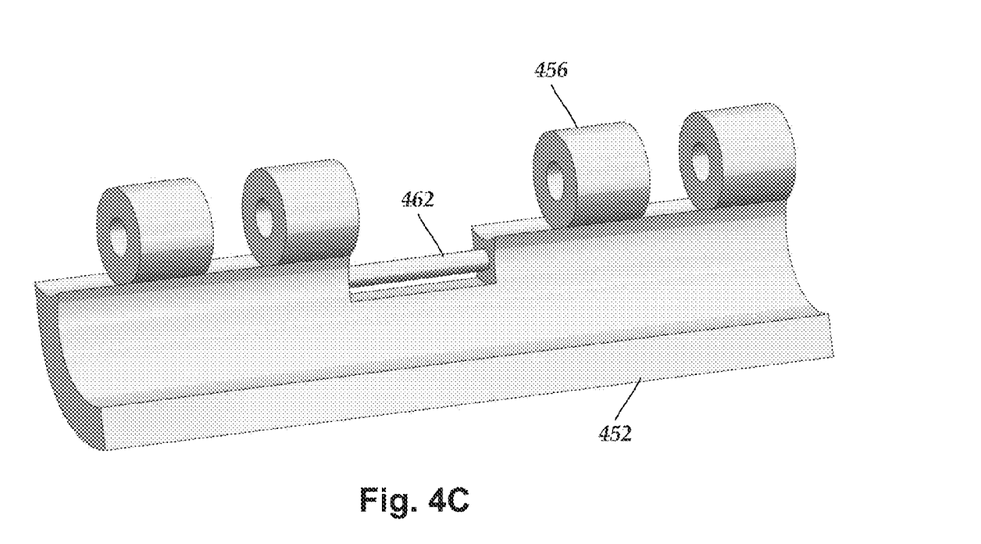
FIG. 4C is a schematic bottom perspective view of one embodiment of an anchor shell of the lead anchor of FIG. 4A (it will be recognized that the other anchor shell of the lead anchor can be identical to the illustrated anchor shell of FIG. 4C), according to the invention.
Figure 4D:
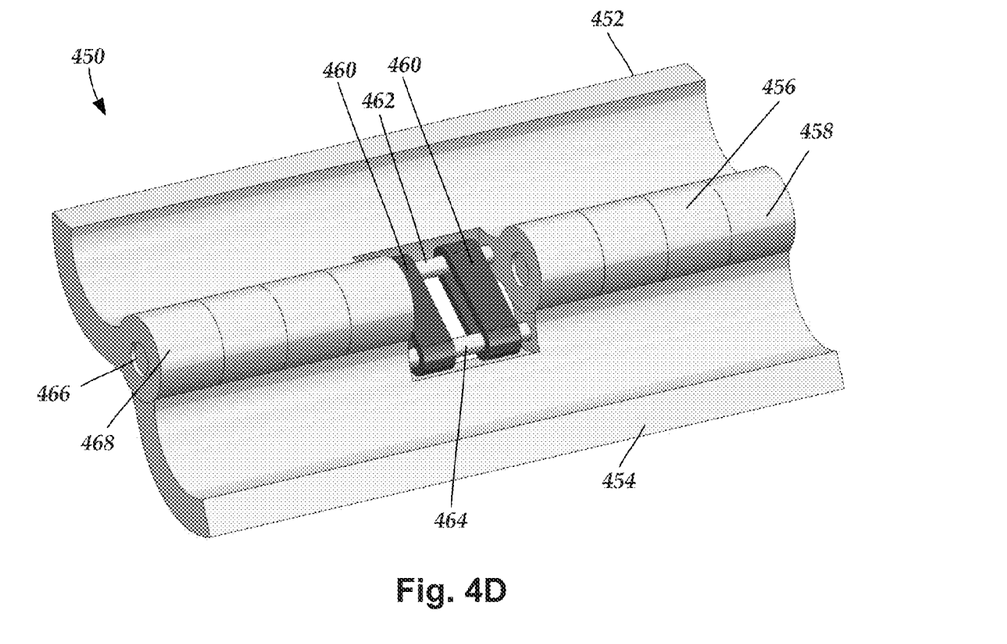
FIG. 4D is a schematic top perspective view of the lead anchor of FIG. 4A in the open position, according to the invention.
Figure 5A:
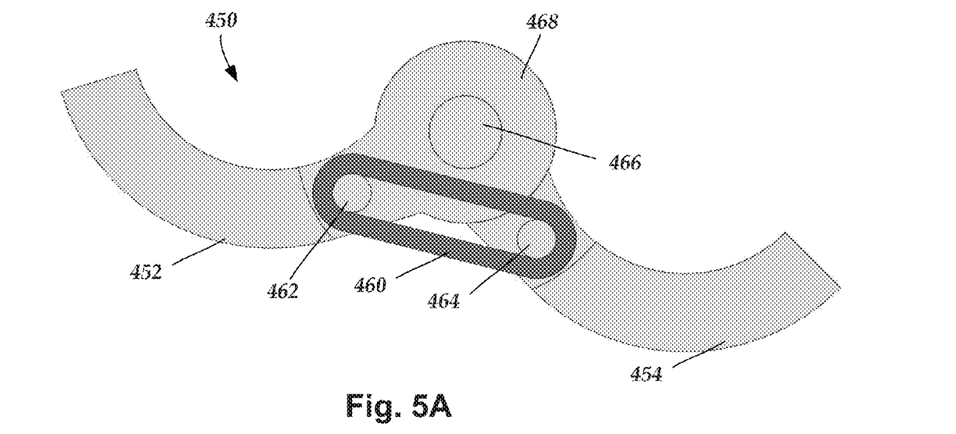
FIG. 5A is a schematic lateral cross-sectional view of the lead anchor of FIG. 4A in the open position, according to the invention.
Figures 5B, 5C:
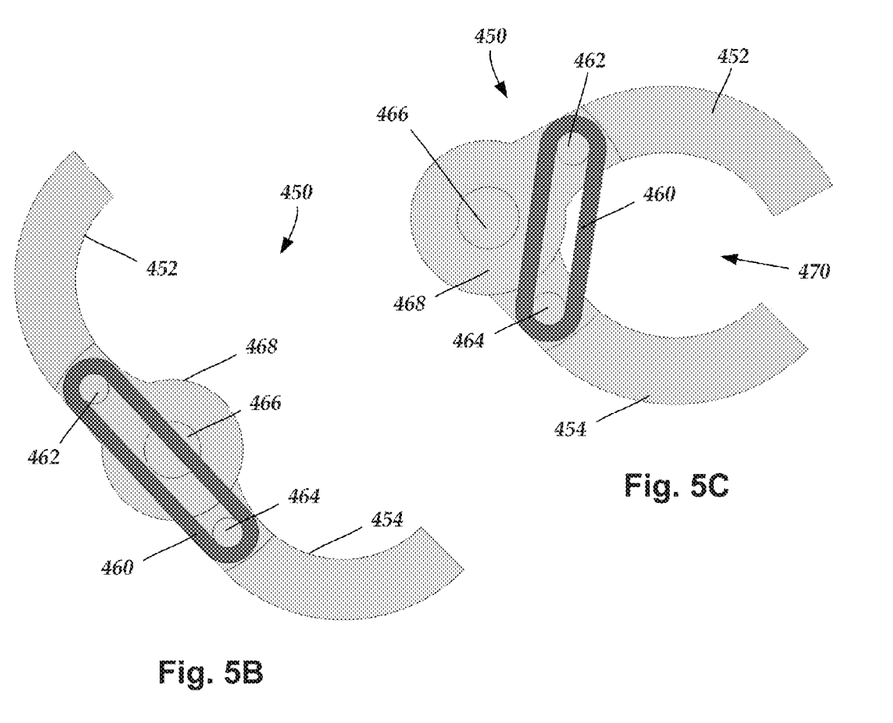
FIG. 5B is a schematic lateral cross-sectional view of the lead anchor of FIG. 4A in the an intermediate position between the open position and the closed position, according to the invention.
FIG. 5C is a schematic lateral cross-sectional view of the lead anchor of FIG. 4A in the closed position, according to the invention.
Figure 6A:
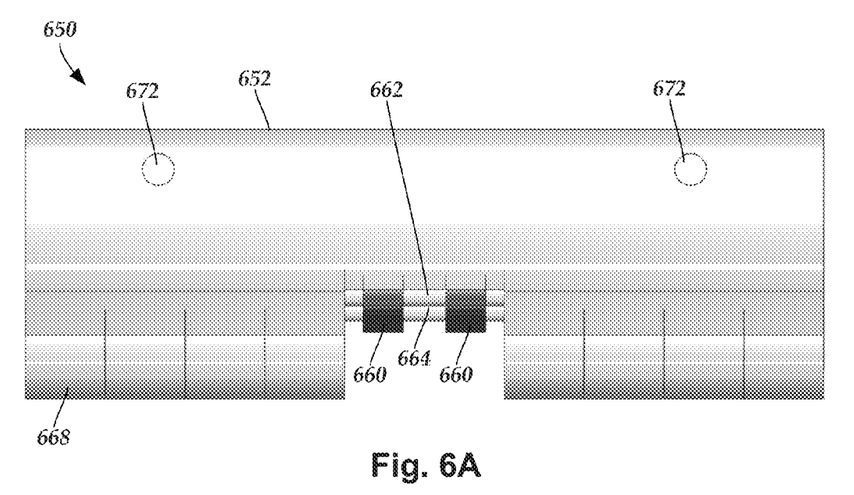
FIG. 6A is a schematic top view of another embodiment of a lead anchor with tension elements and suture openings, according to the invention.
Figure 6B:
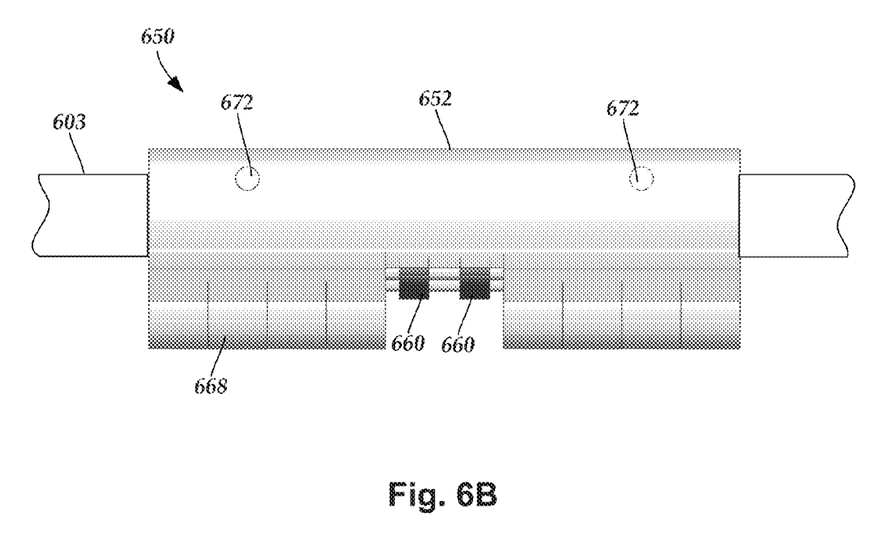
FIG. 6B is a schematic top view of the lead anchor of FIG. 6A with a portion of a lead disposed in the lead anchor, according to the invention.

FIGS. 4A-4D, and 5A-5C illustrate one embodiment of the lead anchor, and FIGS. 6A-6B illustrate another embodiment of the lead anchor.

FIG. 4A illustrates one embodiment of a lead anchor in a closed position. The lead anchor 450 includes two anchor shells 452, 454 disposed opposite each other. Each of the anchor shells 452, 454 is made of any suitable biocompatible material, for example, a plastic or polymer, such as, silicone, polyvinylchloride, polyurethane, or the like; a biocompatible metal or alloy, such as titanium or titanium alloys, nickel, aluminum, stainless steel, copper, gold, silver, platinum or alloys thereof, or any other suitable biocompatible material or combination of materials. In at least some embodiments, the anchor shells 452, 454 are made of the same material. In at least some embodiments, the anchor shells 452, 454 are made of different materials.

Furthermore, it may be useful for any or all parts of the lead anchor 450 to be made of, or incorporate, a radiopaque material, so that it is visible using fluoroscopy or other forms of X-ray imaging.

In some embodiments, each of the anchor shells 452, 454 may have a shape that is a substantially curved arch when viewed in a cross-section taken perpendicular to a longitudinal or central axis of the shells 452, 454. Thus, each of the anchor shells 452, 454 can be formed as a portion of a cylinder, and can be configured to hold the lead such that a longitudinal or central axis of the lead corresponds with or is substantially parallel to the longitudinal or central axis of the anchor shells 452, 454. It will be recognized, however, that other shapes are also suitable for the anchor shells 452, 454, including a C-shape, L-shape, or the like. The anchor shells 452, 454 may have the same shape or can be mirror images with respect to each other. In other embodiments, the anchor shells 452, 454 have different shapes or different cross-sections relative to each other. In some embodiments, both the anchor shells 452, 454 combine to form a shape such as, but not limited to, an oblong, rectangular, elliptical shape, or the like.

Although not shown, a hard stop structure can be incorporated in or attached to one or both of the anchor shells 452, 454 in order to prevent relative rotation beyond a predetermined limit(s) (e.g., between an opened position and/or closed position). For example, outer surfaces of the anchor shells 452, 454 can be configured to touch each other when the anchor shells 452, 454 are rotated to the opened position, thereby providing a limit beyond which the anchor shells 452, 454 are prevented from further opening. Other structures, including bumper structures, slanted surfaces, non-slanted surfaces, attached structures, or adjustable structures such as screws and the like, could be provided on the outer surface of one or both of the anchor shells 452, 454 to provide the hard stop.

In at least some embodiments, each of the anchor shells 452, 454 is an elongated member having a width smaller than its length. Here, width of the anchor shell is measured as a maximum measurement perpendicular to a longitudinal or central axis passing along the length of the shell. In some embodiments, each of the anchor shells 452, 454 has corresponding width greater than, or equal to that of the corresponding length. In at least some embodiments, the anchor shells 452, 454 have different longitudinal lengths and the same width, or vice versa. It should be recognized and understood that the anchor shells 452, 454 may be different in dimensions.

The anchor shells 452, 454 define a lead channel 470 between the first anchor shell 452, and the second anchor shell 454. In at least some embodiments, the lead channel 470 forms a tube-like channel extending along the longitudinal length of the anchor shell. The lead channel 470 may be configured to receive the lead laterally (i.e., by side-loading). The lead channel 470 may have a diameter relatively smaller than that of the lead such that the lead may be compressed within the lead channel 470 in the closed position, thereby engaging and securing the lead within the lead anchor. In at least some embodiments, the lead channel 470 may form a friction fit with the lead when the anchor shells 452, 454 are in the closed position.

The lead channel 470 may have a cross-section that is substantially circular and extending along the length of the anchor shell. It is contemplated that the lead channel 470 may also have a cross-section in the shape of an ovoid, or substantially like a groove, or furrow, or any other suitable shape that is large enough to house a particular lead.

In at least some embodiments, the lead channel 470 is defined so that the lead passes along a straight path formed in the anchor shells 452, 454. In other embodiments, the lead channel 470 may be defined by an angled path formed in the anchor shells 452, 454, for attachment to a similarly angled lead. In some embodiments, the lead channel 470 may be defined as a curved or non-linear path formed in the anchor shells 452, 454. In some embodiments, the lead channel 470 may include interior threads, ridges, micro patterns, or another suitable roughening of the surface of the lead channel 470 for better engagement with a lead.

Each of the anchor shells 452, 454 includes one or more hinge elements, such as hinge elements 456, 458, respectively. Each of the hinge elements 456, 458 may be made from similar materials as that of the anchor shells 452, 454.

In some embodiments, the hinge elements 456, 458 may have a shape that is substantially cylindrical with a circular cross section. It will be recognized, however, that other cross-sectional or lengthwise shapes are also suitable including a rectangular, triangular, oblong, elliptical shape, or the like.

In some embodiments, the hinge elements 456, 458 are elongated members having an aperture extending along a longitudinal axis of the hinge elements 456, 458. The aperture of the hinge elements 456, 458 has substantial dimensions that are configured to receive a hinge pin 466.

The first hinge element 456 is attached to an edge along the longitudinal axis of the length of the first anchor shell 452 (more clearly shown in FIG. 4C). A number of hinge elements are located at a substantial distance from each other on the edge of the anchor shell. There is a space between two adjacent hinge elements. In at least some embodiments, the number of the hinge elements varies depending upon length of the anchor shell and/or size of the hinge elements. For example, the anchor shell may have a substantially large number of narrow hinge elements or a relatively smaller number of wide hinge elements. Likewise, one or more of the second hinge elements 458 are attached to an edge along the longitudinal axis of the length of the second anchor shell 454.

The hinge elements 456, 458 can be continuously formed such that they are an integral portion of corresponding anchor shells 452, 454. Alternatively, the hinge elements 456, 458 can be attached to the anchor shells 452, 45. For example, methods such as welding, or the like; adhesives such as poly(glycerol-co-sebacate acrylate), or the like; fasteners such as a pin, screw, or the like, or any other suitable methods or materials can be used to attach the hinge elements 456, 458 to the anchor shells 452, 454.

In at least some embodiments, the hinge elements 456, 458 are positioned on the edges of the anchor shells 452, 454 respectively. As one example, the first hinge element 456 and the second hinge element 458 combine to form a hinge 468 as the first hinge element 456 fits between two spaced apart second hinge elements 458, and vice versa. In this example, the hinge 468 includes an arrangement in succession of the second hinge element 458 and the first hinge element 456, with such arrangement repeating along a length and edge of the anchor 450. In at least some embodiments, the first hinge element 456 is followed by two consecutive second hinge elements 458, and vice versa to form another arrangement of the hinge elements 456, 458. It will be recognized, however that any suitable number of the first hinge elements 456 may be followed by any suitable number of the second hinge elements 458, and vice versa, thereby forming the hinge 468. A hinge pin 466 passes through the apertures of the first and second hinge elements 456, 458. The first and second anchor shells 452, 454 are aligned such that the apertures of the first and second hinge elements 456, 458 form a lumen of the hinge 468.

A hinge pin 466 is loaded into the lumen of the hinge 468 to complete the hinge 468. The hinge pin 466 may be formed, for example, as a rod having a cross-section that is substantially circular. The hinge pin 466 may be made from similar materials as that of the anchor shells 452, 454. In some embodiments, such as that illustrated in FIG. 4A, two (or more) hinge pins may be used.

The hinge pin 466 is an elongated member having a substantial length and thickness configured to completely occupy the space of the lumen of the hinge 468 thereby preventing occurrence of a loose connection between the hinge elements 456, 458, and holding the hinge 468 intact and tight. The hinge pin 466 is shown as a rod-like structure, but can be formed in different manners which may include, but are not limited, to a nail, a screw, a bolt, a pin, a metal wire, thread, or the like.

In at least some embodiments, the hinge pin 466 is inserted straight into the lumen of the hinge 468 in a linear direction, and fits into the lumen of the hinge 468. In at least some embodiments, the hinge pin 466 has a substantial threaded portion and an inner surface of the hinge 468 is threaded In at least some embodiments, the inner surface of the hinge 468 includes interior threads, ridges, micro patterns, or another suitable roughening of the surface of the hinge 468 for better engagement with the hinge pin 466.

In at least some embodiments, a first rod 462 is disposed between two portions of the first anchor shell 452. Likewise, a second rod 464 is disposed between two portions of the second anchor shell 454. It will be understood that any suitable number of rods may be disposed between the portions of the anchor shells. The rods 462, 464 may be made from similar materials as that of the anchor shells 452, 454. Other examples of suitable rods may include a pin, nail, screw, or any other elongated member.

The rods 462, 464 can be positioned in a cutout formed in each of the anchor shells 452, 454. The cutout may be formed in the anchor shells 452, 454 by any suitable molding or machining method. In at least some embodiments, the cutout can be formed in a substantial middle portion of the anchor shells 452, 454 by methods including machining, casting, extrusion molding, injection molding, or any other known method. When the anchor shells 452, 454 are formed by casting or molding, specific structures, including the cutout, can be further machined into the molded or cast body by known techniques, such as laser cutting, sand/water cutting, machining, or other known techniques.

The rods 462, 464 are attached to opposing surfaces of the anchor shell that define the cutout by any suitable attaching mechanisms or methods. Examples of such mechanisms and methods include, but are not limited to, formation as part of the anchor shell via, for example, injection or other molding techniques, attachment via biocompatible adhesives such as poly(glycerol-co-sebacate acrylate); welding; fasteners such as a screw, a pin, a nail, or the like; or any other suitable method or device.

When the anchor shells 452, 454 are combined, the rods 462, 464 may be parallel with respect to each other. In such an arrangement, the rods 462, 464 are oriented along and parallel with the longitudinal axis of the anchor shells 452, 454, respectively. In at least some embodiments, the rods 462, 464 run straight along the longitudinal axis of the anchor shells 452, 454 and the cutout. In at least some embodiments, multiple rods may be located in the cutout such that a stack of rods is formed across the cutout.

One or more tensioning elements 460 are employed to bias the rods 462, 464 to be closer to each other in either the open position or close position. The tensioning element 460 may be elastic such that the tensioning element 460 is capable of being elongated, and is biased to return to its original shape when elongated.

The tensioning element 460 may form a closed loop such as a band when disposed around the rods 462, 464. The band may have any suitable shape such as oblong, circular, or the like.

The tensioning element 460 may be formed from various biocompatible materials that are elastic, flexible, and strong such that the tensioning element 460 does not break while elongating. Examples of such biocompatible materials may include but are not limited to polymers such as rubber, silicone or the like; copolymers such as ABA triblock, or the like; or any other suitable elastomeric biocompatible material that is well known in the art. In at least some other embodiments, the tensioning element 460 is a spring that may be made from biocompatible elastic materials such as stainless steel, titanium, titanium alloys, or any other suitable biocompatible material. Any suitable number of tensioning elements 460 may be employed including one, two, three, or more tensioning elements. The tensioning element 460 is disposed around the rods 462, 464.

As shown in FIG. 4A, the anchor shells 452, 454 are in the closed position. Outer edges of each of the anchor shells 452, 454 parallel to the edges holding the hinge elements 456, 458 optionally touch each other when in the closed position.

After a portion of the lead is side loaded into the lead channel 470 when the anchor shells 452, 454 are in the open position, the anchor shells 452, 454 can move against bias of the tensioning member 460 to the closed position, thereby providing a grip on the portion of the lead disposed in the lead channel 470. The tensioning element 460 supports the anchor shells 452, 454 in gripping the portion of the lead in the lead channel 470 by biasing the anchor shells 452, 454 towards each other (once the anchor shells 452, 454 pass a predetermined position with respect to each other from the opened to closed position) thus preventing the anchor shells 452, 454 from spontaneously opening when in the closed position. Hence, disengagement of the lead in the lead channel 470 is resisted. As shown in FIG. 4B, the illustrated embodiment of lead anchor 450 is shaped as a C-shaped structure formed by combining and closing the anchor shells 452, 454 to engage a lead within the C-shaped structure. The tensioning element 460 extends substantially perpendicular with respect to a longitudinal axis of the anchor shells 452, 454. The hinge pin 466 is loaded into the lumen of the hinge 468 of the anchor shells 452, 454.

FIG. 4C illustrates one embodiment of the anchor shell 452 of the lead anchor 450. It will be recognized the other anchor shell of the lead anchor 450 can be identical to the illustrated anchor shell 452. As clearly depicted, the first hinge element 456 is disposed on the edge along the longitudinal axis of the first anchor shell 452. A number of hinge elements 456 may be disposed on the edge of the first anchor shell 452 at a distance from each other. The first rod 462 is located in the cutout of the first anchor shell 452.

FIG. 4D is a schematic top view of the lead anchor 450 of FIG. 4A in the open position. In the open position, free edges of the anchor shells 452, 454 are completely separated from each other. The anchor shells 452, 454 can receive the lead laterally for side-loading of the lead. The tensioning element 460 is biased towards maintaining the anchor shells 452, 454 in the open position.

FIG. 5A depicts the lead anchor 450 of FIG. 4A in the open position. In the open position, the tensioning element 460 is biased towards maintaining the anchor shells 452, 454 in the open position. The anchor shells 452, 454 are moved to an intermediate position by elongating the tensioning element 460, as shown in FIG. 5B. The tensioning element 460 requires substantial energy to move the anchor shells 452, 454 to the intermediate position. Further, the anchor shells 452, 454 are moved to the closed position by reducing the elongation of the tensioning element 460, as shown in FIG. 5C. In the closed position, the tensioning element 460 is biased towards maintaining the anchor shells 452, 454 in the closed position. The tensioning element 460 is elongated to less extent in the closed position as compared to that in the intermediate position. Hence, the tensioning element 460 is in a lower energy state in both the closed position and the open position as compared to that in the intermediate state.

FIG. 6A is a schematic top view of another embodiment of a lead anchor 650 with a tensioning element 660 and a suture opening 672. The lead anchor 650 includes two anchor shells that include hinge elements which are combined to form a hinge 668. The tensioning element 660 is coupled to the anchor shells by being disposed around two rods 662, 664. The rods 662, 664 are disposed in a cutout formed in the anchor shells. Except as described below, the design and other functional considerations described with respect to the lead anchor 450 can also apply to the lead anchor 650.

In at least some embodiments, the first anchor shell 652 defines one or more suture openings 672 through the first anchor shell 652. However, it will be contemplated that one or both of the anchor shells may define one or more suture openings 672 through the anchor shells.

The suture opening 672 has a cross-section that is substantially circular. However, the suture opening 672 may have other cross-sectional shapes, such as rectangular, square, triangular, ovoidal, or the like. In other embodiments, the suture opening 672 can be formed as a groove, a stub, an eyelet, a ridge, an opening, a bore, or other suitable structure for suturing the lead anchor 650 to the fascia, ligament, or other tissue or body structure. The suture may be wrapped around a portion of the lead anchor 650 to further hold the anchor shells in the closed position.

A suture or other connective structure may extend through the suture opening 672 to suture or otherwise connect the lead anchor to the patient tissue. The diameter of the suture opening 672 may depend on thickness of the suture, the suture inserter, or dimension of other connective structure used with anchor 650. A suture inserter such as a needle or the like can be used to introduce and advance the suture into the suture opening 672. In at least some embodiments, the suture is a thread, wire, silk, or any other suitable member that has capability to suture the lead anchor 650 to the lead. In other embodiments, a staple, barb or other connective structure can be used in connection with the suture opening in order to attach the anchor 650 to tissue of a patient.

As shown in FIG. 6B, a lead 603 can be side-loaded into a lead channel defined by the anchor shells of the lead anchor 650.

A method of implanting the electrical stimulation lead includes a number of consecutive, non-consecutive, simultaneous, non-simultaneous, or alternative steps. For instance, the method includes provide the lead anchor with the first and second anchor shells in the open position. A portion of a stimulation lead is side-loaded into the lead channel of the anchor shells. Thereafter, the first and second anchor shells are squeezed together, thereby closing the first and second anchor shells to the closed position to lock the stimulation lead in the lead anchor. To achieve the closed position, the first and second anchor shells transition from the open position to an intermediate position by elongating at least one tensioning element. The first and second anchor shells transition from the intermediate position to the closed position by reducing the elongation of the elongated tensioning element, thereby reducing the tension in the tensioning element. The method further includes suturing the lead anchor to the tissue using one or more suture openings of each of the first and second anchor shells.

It will be recognized that the lead anchor may also be operated to release the lead by moving from the closed position to the open position.

Figure 7:
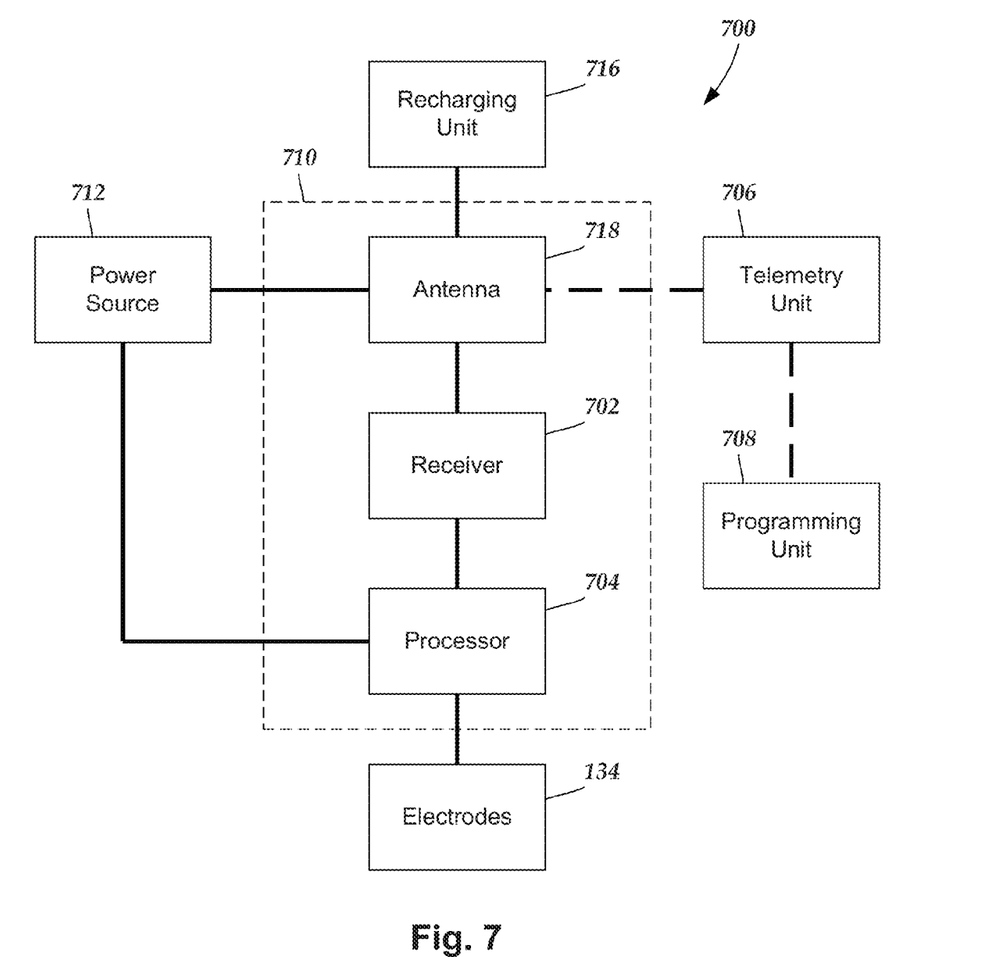
FIG. 7 is a schematic overview of one embodiment of components of a stimulation system, including an electronic subassembly disposed within a control module, according to the invention.

FIG. 7 is a schematic overview of one embodiment of components of an electrical stimulation system 700 including an electronic subassembly 710 disposed within a control module. It will be understood that the electrical stimulation system can include more, fewer, or different components and can have a variety of different configurations including those configurations disclosed in the stimulator references cited herein.

Some of the components (for example, a power source 712, an antenna 718, a receiver 702, and a processor 704) of the electrical stimulation system can be positioned on one or more circuit boards or similar carriers within a sealed housing of an implantable pulse generator, if desired. Any power source 712 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 718 or a secondary antenna. The external power source can be in a device that is mounted on the skin of the user or in a unit that is provided near the user on a permanent or periodic basis.

If the power source 712 is a rechargeable battery, the battery may be recharged using the optional antenna 718, if desired. Power can be provided to the battery for recharging by inductively coupling the battery through the antenna to a recharging unit 716 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 704 is generally included to control the timing and electrical characteristics of the electrical stimulation system. For example, the processor 704 can, if desired, control one or more of the timing, frequency, strength, duration, and waveform of the pulses. In addition, the processor 704 can select which electrodes can be used to provide stimulation, if desired. In some embodiments, the processor 704 selects which electrode(s) are cathodes and which electrode(s) are anodes. In some embodiments, the processor 704 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 708 that, for example, allows modification of pulse characteristics. In the illustrated embodiment, the processor 704 is coupled to a receiver 702 which, in turn, is coupled to the optional antenna 718. This allows the processor 704 to receive instructions from an external source to, for example, direct the pulse characteristics and the selection of electrodes, if desired.

In one embodiment, the antenna 718 is capable of receiving signals (e.g., RF signals) from an external telemetry unit 706 which is programmed by the programming unit 708. The programming unit 708 can be external to, or part of, the telemetry unit 706. The telemetry unit 706 can be a device that is worn on the skin of the user or can be carried by the user and can have a form similar to a pager, cellular phone, or remote control, if desired. As another alternative, the telemetry unit 706 may not be worn or carried by the user but may only be available at a home station or at a clinician's office. The programming unit 708 can be any unit that can provide information to the telemetry unit 706 for transmission to the electrical stimulation system 700. The programming unit 708 can be part of the telemetry unit 706 or can provide signals or information to the telemetry unit 706 via a wireless or wired connection. One example of a suitable programming unit is a computer operated by the user or clinician to send signals to the telemetry unit 706.

The signals sent to the processor 704 via the antenna 718 and the receiver 702 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 700 to cease operation, to start operation, to start charging the battery, or to stop charging the battery. In other embodiments, the stimulation system does not include the antenna 718 or receiver 702 and the processor 704 operates as programmed.

Optionally, the electrical stimulation system 700 may include a transmitter (not shown) coupled to the processor 704 and the antenna 718 for transmitting signals back to the telemetry unit 706 or another unit capable of receiving the signals. For example, the electrical stimulation system 700 may transmit signals indicating whether the electrical stimulation system 700 is operating properly or not or indicating when the battery needs to be charged or the level of charge remaining in the battery. The processor 704 may also be capable of transmitting information about the pulse characteristics so that a user or clinician can determine or verify the characteristics.

The above specification provides a description of the invention and its manufacture and use. Since many embodiments of the invention can be made without departing from the spirit and scope of the invention, the invention also resides in the claims hereinafter appended.

What is claimed as new and desired to be protected by Letters Patent of the United States is:

1. An implantable lead anchor, comprising:
   a first anchor shell comprising a first hinge element;
   a second anchor shell disposed opposite the first anchor shell and comprising a second hinge element, the first and second anchor shells defining a lead channel between the first and second anchor shells and the first and second hinge elements forming a hinge; and
   at least one tensioning element coupled to the first and second anchor shells, wherein each of the at least one tensioning element is configured and arranged to increase in tension upon elongation;
   wherein the first and second anchor shells and the at least one tensioning element are configured and arranged to provide an open position and a closed position, wherein, in the open position, a lead can be side loaded into the lead channel and, in the closed position, the first and second anchor shells grip a portion of the lead disposed in the lead channel and, in combination with the at least one tensioning element, resist disengagement of the lead from the lead anchor, wherein the lead anchor is configured and arranged to move between the open position and the closed position using the hinge and the lead anchor further defines an intermediate position between the open position and the closed position in which, in the intermediate position, the at least one tensioning element is more elongated than in both the open position and the closed position.

2. The implantable lead anchor of claim 1, the at least one tensioning element is a plurality of tensioning elements.

3. The implantable lead anchor of claim 1, wherein the first anchor shell comprises a first rod and the second anchor shell comprises a second rod and the at least one tensioning element is in contact with the first and second rods.

4. The implantable lead anchor of claim 3, wherein the first anchor shell comprises a first portion and a second portion, wherein the first rod is disposed between the first and second portions of the first anchor shell.

5. The implantable lead anchor of claim 1, wherein the first and second anchor shells are identical.

6. The implantable lead anchor of claim 1, further comprising at least one pin disposed within the first hinge element and the second hinge element.

7. The implantable lead anchor of claim 1, wherein each of the at least one tensioning element is elastomeric.

8. An implantable lead anchor, comprising:
   a first anchor shell comprising a first hinge element;
   a second anchor shell disposed opposite the first anchor shell and comprising a second hinge element, the first and second anchor shells defining a lead channel between the first and second anchor shells and the first and second hinge elements forming a hinge; and
   at least one tensioning element coupled to the first and second anchor shells, wherein each of the at least one tensioning element is configured and arranged to increase in tension upon elongation;
   wherein the first and second anchor shells and the at least one tensioning element are configured and arranged to provide an open position and a closed position, wherein, in the open position, a lead can be side loaded into the lead channel and, in the closed position, the first and second anchor shells grip portion of the lead disposed in the lead channel and, in combination with the at least one tensioning element, resist disengagement of the lead from the lead anchor, wherein the lead anchor is configured and arranged to move between the open position and the closed position using the hinge and the lead anchor further defines an intermediate position between the open position and the closed position in which, in the intermediate position, the at least one tensioning element is more elongated than in both the open position and the closed position, wherein each of the at least one tensioning element comprises an elastomeric polymer band.

9. The implantable lead anchor of claim 1, wherein the at least one tensioning element comprises a spring.

10. An implantable lead anchor, comprising:
a first anchor shell comprising a first hinge element;
a second anchor shell disposed opposite the first anchor shell and comprising a second hinge element, the first and second anchor shells defining a lead channel between the first and second anchor shells and the first and second hinge elements forming a hinge; and
at least one tensioning element coupled to the first and second anchor shells, wherein each of the at least one tensioning element is configured and arranged to increase in tension upon elongation;
wherein the first and second anchor shells and the at least one tensioning element are configured and arranged to provide an open position and a closed position, wherein, in the open position, a lead can be side loaded into the lead channel and, in the closed position, the first and second anchor shells grip a portion of the lead disposed in the lead channel and, in combination with the at least one tensioning element, resist disengagement of the lead from the lead anchor, wherein the lead anchor is configured and arranged to move between the open position and the closed position using the hinge and the lead anchor further defines an intermediate position between the open position and the closed position in which, in the intermediate position, the at least one tensioning element is more elongated than in both the open position and the closed position, wherein the first anchor shell defines at least one suture opening therethrough.

11. The implantable lead anchor of claim 1, wherein the first and second anchor shells have different longitudinal lengths.

12. A kit, comprising:
the implantable lead anchor of claim 1; and
at least one electrical stimulation lead, wherein the implantable lead anchor is configured and arranged to receive a portion of one of the at least one electrical stimulation lead in the lead channel.

13. The kit of claim 12, further comprising a control module coupleable to the at least one electrical stimulation lead.

14. The kit of claim 13, further comprising a lead extension coupleable to the lead and to the control module.

15. A method of implanting an electrical stimulation lead, the method comprising:
side loading a portion of an electrical stimulation lead into the lead channel of the implantable lead anchor of claim 1, wherein the first and second anchor shells of the implantable lead anchor are in the open position; and
closing the first and second anchor shells to the closed position to lock the first electrical stimulation lead in the implantable lead anchor.

16. The method of claim 15, wherein closing the first and second anchor shells comprises squeezing the first and second anchor shells together.

17. The method of claim 15, wherein closing the first and second anchor shells comprises transitioning from the open position to the intermediate position by elongating the at least one tensioning element.

18. The method of claim 17, wherein closing the first and second anchor shells further comprises transitioning from the intermediate position to the closed position by reducing elongation of the at least one tensioning element.

19. The method of claim 15, wherein at least one of the first and second anchor shells defines at least one suture opening, the method further comprising suturing the implantable lead anchor to tissue using the at least one suture opening of each of the first and second shells.

20. The method of claim 15, further comprising opening the first and second anchor shells prior to side loading the portion of the electrical stimulation lead.

* * * * *